United States Patent [19]

Jorgensen

[11] Patent Number: 5,140,008

[45] Date of Patent: Aug. 18, 1992

[54] HUMAN GROWTH HORMONE UNIT DOSE FOR THE TREATMENT OF INTOXICATED INDIVIDUALS

[75] Inventor: Karin D. Jørgensen, Vedbaek, Denmark

[73] Assignee: Novo Nordisk A/S, Bagsvaerd, Denmark

[21] Appl. No.: 262,466

[22] Filed: Oct. 25, 1988

Related U.S. Application Data

[63] Continuation-in-part of Ser. No. 32,053, Mar. 27, 1987, Pat. No. 4,816,439.

[51] Int. Cl.$^5$ ............................................. A61K 37/36
[52] U.S. Cl. ..................................... 514/12; 514/810; 514/811; 514/8
[58] Field of Search ................... 530/324, 350, 399; 514/12, 810, 811

[56] References Cited

U.S. PATENT DOCUMENTS

| | | | |
|---|---|---|---|
| 4,452,775 | 6/1984 | Kent | 514/12 |
| 4,816,439 | 3/1989 | Jorgensen | 514/12 |
| 4,816,568 | 3/1989 | Hamilton, Jr. | 530/362 |

FOREIGN PATENT DOCUMENTS

0085036A1  8/1983  European Pat. Off. .

OTHER PUBLICATIONS

Powell-Jackson et al., *The Lancet*, 244–246 (1985).
Williams, *Pharmacotherapy*, 6, 311–318 (1986).

*Primary Examiner*—F. T. Moezie
*Attorney, Agent, or Firm*—Ladas & Parry

[57] ABSTRACT

Human growth hormone is used for the treatment of individuals who are intoxicated with poisonous substances of the type which is degraded in the liver by microsomal enzymes, such as hexobarbiturates or alcohol. Unit dose preparations containing a pharmacologically active dose of human growth hormone is used for treating intoxicated individuals.

3 Claims, 1 Drawing Sheet

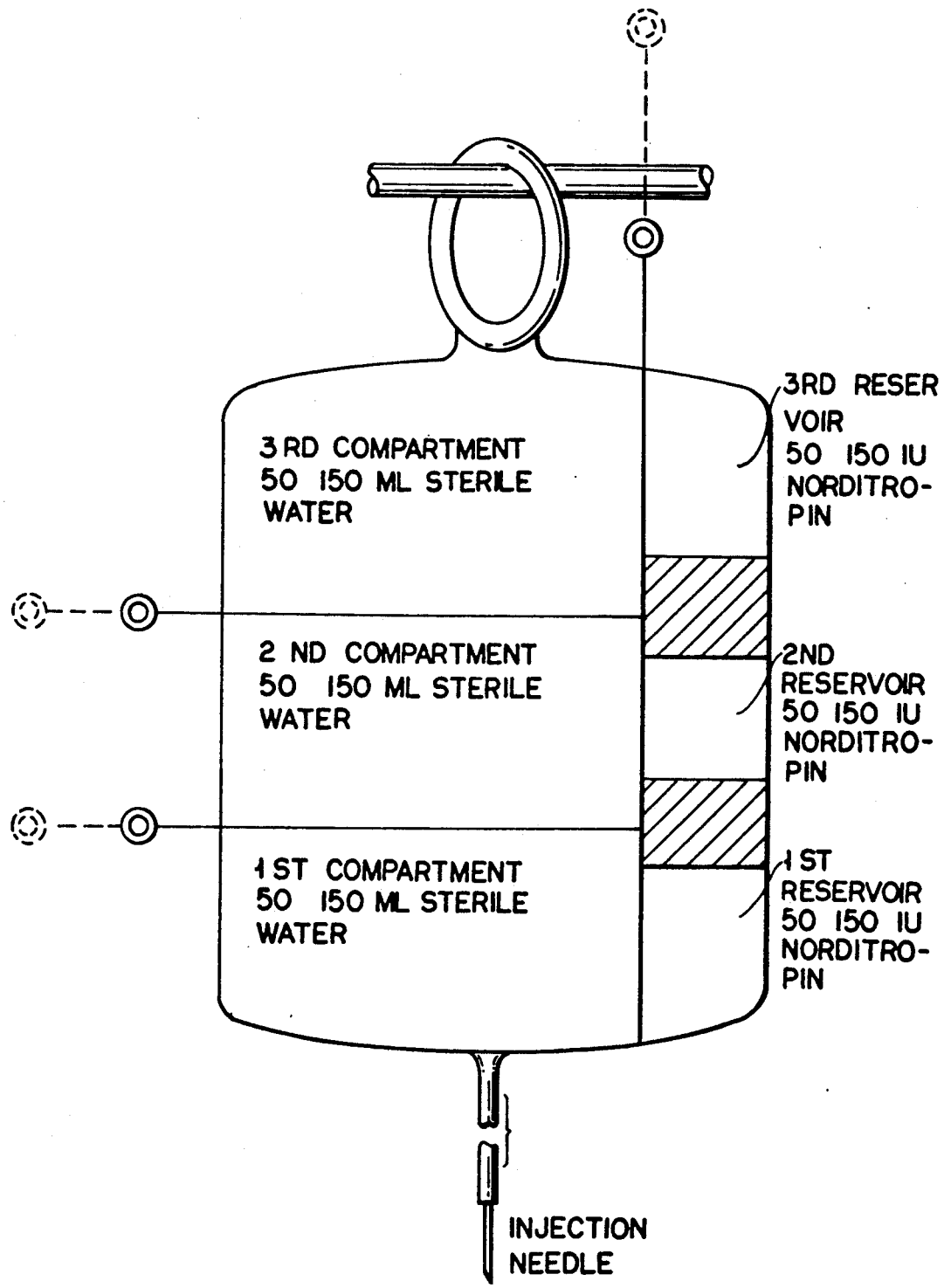

HUMAN GROWTH HORMONE UNIT DOSE FOR THE TREATMENT OF INTOXICATED INDIVIDUALS

This is a continuation-in-part of application Ser. No. 07/032,053 filed on Mar. 27, 1987, now U.S. Pat. No. 4,816,439, issued Mar. 28, 1989. The invention relates to the use of human growth hormone for the treatment of individuals who are intoxicated with poisonous substances of the type which is degraded in the liver by microsomal enzymes.

Furthermore the invention relates to a preparation for treating such intoxicated individuals. Medicine intoxicated patients, such as individuals who have taken overdoses of soporifics, for example, barbiturates, have previously been treated with pumping outs and respiration.

So far, however, there has been no actual antidote against toxic substances, for example, barbituraes, which are absorbed into the organism and accumulate in the liver where they are slowly degraded enzymatically.

The present invention is based on the observation that the presence of hGH reduces the time in which toxic substances of the type indicated are active. It is thus assumed that the breaking down of toxic substances, for example barbiturates, in the liver may be accelerated through the administration of human growth hormone, hGH. The reason for this effect is not known, but it is assumed that hGH either activates the degradable enzymes or causes increased production of such enzymes.

In accordance herewith the effect of hGH is one which functions in connection with all toxic substances of the type which is mainly absorbed and broken down in the liver.

Apart from barbiturates such toxic substances comprise alcohol. In consequence hGH is suitable for treating alcoholic poisoning.

Any in itself known preparation containing a pharmacologically active dose of hGH may be used for treating intoxicated individuals. The method of administration is not important to the effect achieved, if only it is ensured that the quantity of hGH preparation administered has a certain magnitude. Normally corresponding to a maximum of 100 IU/kg body weight. The preparation may, for example, contain 50–10000 IU of hGH. It may also contain 200–400 ml of sterile water and mineral salts in an amount sufficient to make the preparation isotonic.

The hGH preparation applied may appropriately be administered in injectable doses of 0.1–10 IU/kg body weight, administered at intervals up to 10 times.

Alternatively the hGH preparation may be administered in the form of an infusion preparation where the hGH preparation is continuously being administered to the patient in amounts of appropriately up to 100 IU/kg body weight. This amount should be administered over not more than 1 day, but in certain instances, and if required, the treatment may be continued over a longer period of time.

One method of administration is the use of nasal preparations, for example in spray form, where the hGH preparation contains substances which facilitate the penetration of mucous membranes.

Depending on the method of administration the preparation may contain any suitable vehicles or subsidiary materials of the usual kinds and which may be selected by a person skilled in the art.

In the disclosure which follows, the invention will be illustrated by means of some working examples.

DESCRIPTION OF THE DRAWING

The device shown in the drawing has three reservoirs containing 50 to 150 IU of Norditropin ® in a freeze-dried state.

The Norditropin ® has been freeze-dried with electrolytes corresponding to 50 to 150 ml of a Ringer Lactate infusion liquid, a Ringer Chloride infusion liquid, a Multipel ® infusion liquid or an isotonic NaCl infusion liquid. The Norditropin ® may also be freeze-dried in Norditropin ® buffer.

A reservoir of three compartments each containing 50 to 150 ml of sterile water is provided in connection with the three reservoirs. These three compartments can be caused to communicate with each other, and each communicates with a Norditropin ® reservoir.

A treatment may be initiated by establishing an opening between the first Norditropin ® reservoir and the first compartment of sterile water. The Norditropin ® will be dissolved by this, and when providing connection with an infusion set, 50 to 150 ml of infusion liquid, e.g. Ringer Lactate with 50 to 150 IU of Norditropin ® may now be infused i.v.

If a higher dose of Norditropin ® is desired, an opening is established to the second water compartment and the second Norditropin ® reservoir, and the dosis may likewise be increased with the third compartment plus reservoir. Thus, a total of 150 to 450 IU of Norditropin ® in 150 to 450 ml of Ringer Lactate or another infusion liquid may thus be infused over e.g. 1 hour.

EXAMPLE 1

Biosynthetic human growth hormone, pituitary human growth hormone (Nanormon ®) and pituitary 22K, all manufactured by Nordisk Gentofte A/S, were tested for their effect on the duration of hexobarbital narcosis in mice. The three growth hormone preparations were administered subcutaneously to mice in dosages of 0.25, 2.5 and 25 IU/kg body weight. Nanormon ® buffer was used as placebo.

The freeze-dried materials were dissolved in 3 ml distilled water to obtain isotonic solutions. Further dilutions were made with Nanormon ® buffer. The stock solutions contained 1.4 mg protein/ml (B-hGH), 1.1–1.5 mg/ml (P22K) and 1.6 mg/ml protein (Nanormon ®), and the biological potencies as determined by a preliminary tibia test were 2.0 IU/mg, 1.9 IU/mg and 2.6 IU/mg, respectively.

25 IU/kg, 2.5 IU/kg and 0.25 IU/kg body weight was administered in volumes of 0.2 ml/mouse, i.e. 10 ml/kg body wight subcutaneously in the neck. The same volumes of Nanormon ® buffer was used as placebo.

A 0.4% solution of hexobarbital in distilled water added approximately 10 $\mu$l 5 N NaOH per ml was prepared. NaOH was from the Chemical Control Department. The mice were dosed with 0.5 ml (100 mg/kg) intraperitoneally.

Male and female NMRI mice from Gl. Bomoltgaard, Ry, were acclimatized for 4–7 days before use at 20±1° C., 60±5% relative humidity, air change 16 per hour and light from 7.30 a.m. till 7.30 p.m. The animals had free access to Altromin diet and drinking water and were kept in rectangular polypropylene or Macrolon ® cages with Spanvall beech bedding. When the mice were used, they were 20±2 g and 26–31 days old (male mice), 28–33 days old (female mice).

Each dosage of growth hormone was administered to four groups of 10 mice, the two groups having growth hormone s.c. ½ hour before hexobarbital i.p. and the other two groups having growth hormone 2 hours before hexobarbital dosing. The treatments were randomly assigned to the groups and a placebo group was included each experimental day. During the narcosis the mice were placed on a heated operation table (37° C.) (from Hugo Sachs Elektronik), and the time from disappearance till reappearance of the righting reflex was registered as the sleeping time.

RESULTS

In table 1A and 1B the results ar known for male and female mice respectively, when the growth hormone preparations were administered ½ h before hexobarbital dosing. All three growth hormone preparations caused a significant shortening of the hexobarbital sleeping time (for significance levels see the tables). Effects were observed even after 0.25 iu/kg - nearly therapeutic doses. There were no differences between male and female mice. In all groups the onset of narcosis was within a few minutes after hexobarbital i.p., and it was not changed by the previous dosing of growth hormones. Tables 2A and 2B show the corresponding results for male and female mice when the growth hormones were dosed for 2 h prior to hexobarbital. Apparently the effects of growth hormone are practically absent. This means that the effect is of rather short duration. The mechanism of action is not known, and the effect has not been reported in the literature. As the other pharmacological results do not support in any way a central stimulating action of growth hormone, other explanations may be that growth hormone promotes redistribution of hexobarbital from the brain to other tissues or perhaps causes an induction of the microsomal enzymes in the liver responsible for the oxidative metabolism of barbiturates.

CONCLUSION

Biosynthetic human growth hormone, Nanormon® and pituitary 22K human growth hormone, all decrease the duration of hexobarbital narcosis in mice significantly. Effects are seen even after 0.25 IU/kg body weight (approximately human therapeutic doses). The effect is of rather short duration, less than 2½ hours.

DURATION OF HEXOBARBITAL NARCOSIS IN MICE

The doses of growth hormone were injected subcutaneously 30 minutes before intraperitoneal administration of hexobarbital, 100 mg/kg.

| Treatment | Doses IU/kg b. wt. s.c. | N Mice Sex | Loss of righting reflex, min. after hexobarbital $\bar{X} \pm$ S.E.M. | Reappearance of righting reflex, min after hexobarbital $\bar{X} \pm$ S.E.M. | Duration of narcosis (min.) $\bar{X} \pm$ S.E.M. | Ratio of duration |
|---|---|---|---|---|---|---|
| Placebo | — | 20 male | 3.4 ± 0.2 | 40 ± 3 | 37 ± 2.6 | 1.000 |
| Nanormon ® | 25 | 10 male | 4.0 ± 0.3 | 38 ± 2 | 34 ± 2.2 | 0.919 |
|  | 2.5 | 10 male | 4.0 ± 0.3 | 25 ± 2 | 21 ± 2.1[3] | 0.568 |
|  | 0.25 | 10 male | 3.3 ± 0.3 | 25 ± 3 | 22 ± 2.7[2] | 0.595 |
| Biosynthetic | 25 | 10 male | 4.4 ± 0.3 | 28 ± 2 | 24 ± 2.6[2] | 0.649 |
| human growth | 2.5 | 10 male | 4.5 ± 0.8 | 30 ± 4 | 26 ± 4.5[1] | 0.703 |
| hormone | 0.25 | 10 male | 3.4 ± 0.3 | 31 ± 2 | 28 ± 2.5 | 0.757 |
| Pituitary 22K | 25 | 10 male | 5.3 ± 1.0 | 22 ± 3 | 17 ± 2.5[3] | 0.459 |
|  | 2.5 | 10 male | 4.7 ± 0.3 | 30 ± 5 | 25 ± 4.9[1] | 0.676 |
|  | 0.25 | 10 male | 3.9 ± 0.2 | 29 ± 3 | 26 ± 3.2[1] | 0.703 |

[1] $p < 0.05$,
[2] $p < 0.01$,
[3] $p < 0.001$ (Student's t-test)

DURATION OF HEXOBARBITAL NARCOSIS IN MICE

The doses of growth hormone were injected subcutaneously 30 minutes before intraperitoneal administration of hexobarbital, 100 mg/kg.

| Treatment | Doses IU/kg b. wt. s.c. | N Mice Sex | Loss of righting reflex, min. after hexobarbital $\bar{X} \pm$ S.E.M. | Reappearance of righting reflex, min after hexobarbital $\bar{X} \pm$ S.E.M. | Duration of narcosis (min.) $\bar{X} \pm$ S.E.M. | Ratio of duration |
|---|---|---|---|---|---|---|
| Placebo | — | 20 female | 3.8 ± 0.2 | 43 ± 3 | 39 ± 3.4 | 1.000 |
| Nanormon ® | 25 | 10 female | 4.5 ± 0.5 | 30 ± 5 | 25 ± 4.5[1] | 0.641 |
| . | 2.5 | 10 female | 4.1 ± 0.4 | 29 ± 3 | 26 ± 2.8[1] | 0.667 |
|  | 0.25 | 10 female | 4.3 ± 0.3 | 35 ± 3 | 31 ± 2.9 | 0.795 |
| Biosynthetic | 25 | 10 female | 4.8 ± 0.3 | 25 ± 3 | 20 ± 2.5[2] | 0.513 |
| human growth | 2.5 | 10 female | 3.7 ± 0.3 | 32 ± 3 | 28 ± 3.5 | 0.718 |
| hormone | 0.25 | 10 female | 4.1 ± 0.3 | 34 ± 3 | 30 ± 3.3 | 0.769 |
| Pituitary 22K | 25 | 10 female | 5.3 ± 0.6 | 32 ± 4 | 27 ± 3.8[1] | 0.692 |
|  | 2.5 | 10 female | 3.9 ± 0.4 | 18 ± 1 | 15 ± 1.3[3] | 0.385 |
|  | 0.25 | 10 female | 3.5 ± 0.1 | 34 ± 3 | 31 ± 2.7 | 0.795 |

[1] $p < 0.05$,
[2] $p < 0.01$,
[3] $p < 0.001$ (Student's t-test)

DURATION OF HEXOBARBITAL NARCOSIS IN MICE

The doses of growth hormone were injected subcutaneously 120 minutes before intraperitoneal administration of hexobarbital, 100 mg/kg.

| Treatment | Doses IU/kg b. wt. s.c. | N Mice | Sex | Loss of righting reflex, min. after hexobarbital X ± S.E.M. | Reappearance of righting reflex, min after hexobarbital X ± S.E.M. | Duration of narcosis (min.) X ± S.E.M. | Ratio of duration |
|---|---|---|---|---|---|---|---|
| Placebo | — | 30 | male | 3.3 ± 0.2 | 35 ± 2 | 32 ± 2.5 | 1.000 |
| Nanormon ® | 25 | 10 | male | 3.0 ± 0.3 | 44 ± 5 | 41 ± 5.2 | 1.281 |
| | 2.5 | 10 | male | 2.9 ± 0.4 | 42 ± 4 | 39 ± 3.8 | 1.219 |
| | 0.25 | 10 | male | 4.0 ± 0.2 | 23 ± 1 | 20 ± 1.5[1] | 0.625 |
| Biosynthetic | 25 | 10 | male | 3.4 ± 0.3 | 45 ± 3 | 43 ± 4.0 | 1.344 |
| human growth | 2.5 | 10 | male | 3.1 ± 0.3 | 29 ± 4 | 27 ± 4.5 | 0.844 |
| hormone | 0.25 | 10 | male | 3.7 ± 0.1 | 34 ± 4 | 31 ± 3.6 | 0.969 |
| Pituitary 22K | 25 | 10 | male | 2.9 ± 0.2 | 33 ± 5 | 30 ± 4.9 | 0.938 |
| | 2.5 | 10 | male | 2.8 ± 0.5 | 44 ± 7 | 41 ± 7.1 | 1.281 |
| | 0.25 | 10 | male | 4.0 ± 0.2 | 27 ± 2 | 23 ± 1.7 | 0.719 |

[1] $p < 0.05$ (Student's t-test)

DURATION OF HEXOBARBITAL NARCOSIS IN MICE

The doses of growth hormone were injected subcutaneously 120 minutes before intraperitoneal administration of hexobarbital, 100 mg/kg.

| Treatment | Doses IU/kg b. wt. s.c. | N Mice | Sex | Loss of righting reflex, min. after hexobarbital X ± S.E.M. | Reappearance of righting reflex, min after hexobarbital X ± S.E.M. | Duration of narcosis (min.) X ± S.E.M. | Ratio of duration |
|---|---|---|---|---|---|---|---|
| Placebo | — | 30 | female | 3.7 ± 0.2 | 39 ± 4 | 35 ± 4.0 | 1.000 |
| Nanormon ® | 25 | 10 | female | 3.5 ± 0.3 | 42 ± 5 | 38 ± 4.8 | 1.086 |
| | 2.5 | 10 | female | 3.3 ± 0.2 | 37 ± .6 | 34 ± 6.1 | 0.971 |
| | 0.25 | 10 | female | 3.5 ± 0.2 | 33 ± 6 | 30 ± 5.6 | 0.857 |
| Biosynthetic | 25 | 10 | female | 3.5 ± 0.2 | 38 ± 3 | 35 ± 3.5 | 1.000 |
| human growth | 2.5 | 10 | female | 2.8 ± 0.3 | 35 ± 3 | 32 ± 2.6 | 0.914 |
| hormone | 0.25 | 10 | female | 3.6 ± 0.3 | 35 ± 4 | 32 ± 4.3 | 0.914 |
| Pituitary 22K | 25 | 10 | female | 3.9 ± 0.3 | 37 ± 5 | 33 ± 4.6 | 0.943 |
| | 2.5 | 10 | female | 3.3 ± 0.4 | 33 ± 3 | 30 ± 3.5 | 0.857 |
| | 0.25 | 10 | female | 4.1 ± 0.3 | 17 ± 1 | 13 ± 1.6[2] | 0.371 |

[2] $p < 0.01$ (Student's t-test)

EXAMPLE 2

Experiments were carried out as mentioned in example 1, substituting pentabarbital for hexobarbital.

A similar effect was found, except that it was more pronounced on female mice than on male mice.

I claim:

1. A unit dose preparation for the treatment of individuals intoxicated with poisonous substances that are mainly degraded in the liver, comprising hGH in an amount of 50–10000 IU.

2. Preparation according to claim 1, further comprising at least 100 ml sterile water and additives in an amount sufficient to make the preparation isotonic.

3. Preparation according to claim 1, further comprising 200–400 ml sterile water and mineral salt in an amount sufficient to make the preparation isotonic.

* * * * *